(12) United States Patent
Hamilton et al.

(10) Patent No.: US 7,142,118 B2
(45) Date of Patent: Nov. 28, 2006

(54) MANAGEMENT AND DISTRIBUTION OF SURGICAL SUPPLIES WITHIN AN RFID ENABLED NETWORK

(75) Inventors: John A. Hamilton, Tampa, FL (US); Mary L. McCoy, Tampa, FL (US); Charles Pope, Tampa, FL (US); Joseph A. Largey, Tampa, FL (US)

(73) Assignee: SRI/Surgical Express, Inc., Tampa, FL (US)

( * ) Notice: Subject to any disclaimer, the term of this patent is extended or adjusted under 35 U.S.C. 154(b) by 86 days.

(21) Appl. No.: 10/873,783

(22) Filed: Jun. 22, 2004

(65) Prior Publication Data

US 2005/0280536 A1    Dec. 22, 2005

(51) Int. Cl.
*G06Q 50/00* (2006.01)
*G06F 7/06* (2006.01)

(52) U.S. Cl. .................. 340/572.1; 235/375; 377/5; 705/2; 700/215; 209/3.3

(58) Field of Classification Search ............. 340/572.1, 340/5.9–5.92; 705/2, 22, 28–29; 235/375, 235/385
See application file for complete search history.

(56) References Cited

U.S. PATENT DOCUMENTS

| 4,550,246 | A | | 10/1985 | Markman |
| 5,042,474 | A | * | 8/1991 | Williamson ............ 128/206.12 |
| 5,233,167 | A | | 8/1993 | Markman |
| 5,374,813 | A | * | 12/1994 | Shipp ......................... 235/375 |
| 5,434,775 | A | | 7/1995 | Sims |
| 5,602,538 | A | | 2/1997 | Orthmann |
| 5,687,850 | A | * | 11/1997 | Speckhart et al. ............. 209/2 |
| 5,689,238 | A | | 11/1997 | Cannon, Jr. |
| 5,715,555 | A | * | 2/1998 | Reber et al. .................... 8/158 |
| 5,726,630 | A | | 3/1998 | Marsh |
| 5,785,181 | A | * | 7/1998 | Quartararo, Jr. ............. 209/3.3 |
| 5,794,213 | A | | 8/1998 | Markman |
| 5,910,776 | A | | 6/1999 | Black |
| 5,923,001 | A | * | 7/1999 | Morris et al. ............... 177/245 |
| 5,962,834 | A | | 10/1999 | Markman |

(Continued)

*Primary Examiner*—Jeffery Hofsass
*Assistant Examiner*—Anne V. Lai
(74) *Attorney, Agent, or Firm*—Caesar, Rivise, Bernstein, Cohen & Pokotilow, Ltd.

(57) ABSTRACT

The present invention contributes to advancements in the art of inventory management and distribution by providing a system and method for processing, distributing, and tracking reusable inventory items. Reusable articles, such as surgical garments and accessories, are adapted with radio frequency identification ("RFID") tags having unique identification numbers. A "reader" is used to retrieve stored information from the tags without requiring direct contact or clear line-of-sight. The reusable articles are processed and distributed using an inventory management system wherein lifecycle data is obtained for each reusable article. The reusable articles are distributed to the end users from central processing facilities, used, returned, cleaned, inspected, folded, sterilized, and returned to inventory for re-distribution. Periodic quality control inspections are conducted in response to predetermined usage parameters. The use of RFID tags and a corresponding computer network allows for the acquisition of data corresponding to each reusable article within a distribution system having multiple remote distribution and processing facilities. The acquired data is transmitted to a central computer processing system via a secured wide area computer network for use and analysis. Data processing computer servers at each remote distribution and processing facility electronically linked to a central data processing server provide a fail-safe network for acquired data.

23 Claims, 6 Drawing Sheets

U.S. PATENT DOCUMENTS

| | | |
|---|---|---|
| 5,991,355 A * | 11/1999 | Dahlke ........................ 377/15 |
| 6,354,493 B1 | 3/2002 | Mon |
| 6,535,129 B1 | 3/2003 | Petrick |
| 6,616,034 B1 | 9/2003 | Wu |
| 6,693,539 B1 | 2/2004 | Bowers |
| 6,727,818 B1 * | 4/2004 | Wildman et al. ........ 340/573.1 |
| 7,019,650 B1 * | 3/2006 | Volpi et al. .............. 340/572.1 |
| 2002/0017990 A1 * | 2/2002 | Okamura ................. 340/572.1 |
| 2002/0067263 A1 * | 6/2002 | Tafoya et al. ............ 340/572.1 |
| 2003/0200006 A1 * | 10/2003 | Penkar et al. ................ 700/214 |
| 2004/0220824 A1 * | 11/2004 | Imai et al. ...................... 705/1 |
| 2004/0249497 A1 * | 12/2004 | Saigh et al. ................. 700/216 |
| 2004/0250819 A1 * | 12/2004 | Blair et al. ................... 128/899 |
| 2005/0258961 A1 * | 11/2005 | Kimball et al. ........... 340/572.1 |

* cited by examiner

| Inspector | Date | Start Time | End Time | Hrs:Min | RFID Count | DS* | Ack | Rewash | Repair | Req'd Test | Pass | Fail | Accepted | Avg/Hr |
|---|---|---|---|---|---|---|---|---|---|---|---|---|---|---|
| J. Doe | 2/16/04 | 06.01.53 | 06.37.13 | :35 | 56 | | 2 | 1 | 3 | 2 | 2 | | | |
| J. Doe | 2/16/04 | 05.59.41 | 06.59.42 | :00 | 1 | | | | | | | | | |
| J. Doe | 2/16/04 | 10.34.43 | 11.00.49 | :26 | 44 | | 1 | 13 | 13 | | | | | |
| J. Doe | 2/16/04 | 12.17.51 | 12.42.20 | :24 | 37 | | 1 | 4 | 8 | 2 | 2 | | | |
| J. Doe | 2/16/04 | 13.38.58 | 14.25.41 | :46 | 60 | | 2 | 6 | 11 | | | | | |
| | | | | 2:11 | 198 | — | 6 | 24 | 35 | 4 | 4 | — | 133 | 30 |
| S. Smith | 2/16/04 | 06.41.44 | 07.24.28 | :42 | 118 | | 10 | 1 | 6 | 9 | 9 | | | |
| S. Smith | 2/16/04 | 08.22.25 | 08.27.45 | :05 | 19 | | 4 | 1 | 1 | 2 | 2 | | | |
| S. Smith | 2/16/04 | 10.03.30 | 10.10.50 | :07 | 29 | | 7 | | | 1 | 1 | | | |
| S. Smith | 2/16/04 | 11.57.08 | 12.18.16 | :21 | 67 | | 10 | | | 3 | 3 | | | |
| | | | | 1:15 | 233 | — | 31 | 2 | 7 | 15 | 15 | — | 193 | 154 |

FIG. 7

MANAGEMENT AND DISTRIBUTION OF SURGICAL SUPPLIES WITHIN AN RFID ENABLED NETWORK

CROSS REFERENCE TO RELATED APPLICATIONS

N/A

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

The present invention generally relates to the management of inventory and quality control, and more particularly, to the use of radio frequency identification ("RFID") technology in the management and quality control of reusable inventory throughout predetermined lifecycles across multiple locations and processes.

2. Description of Related Art

The number of surgical procedures performed at hospitals and surgical facilities has increased dramatically in recent years. As the annual number of surgical procedures has increased, hospitals and surgical facilities have struggled to manage the supply and processing of surgical supplies, particularly reusable articles such as surgical gowns and drapes. As a result hospitals and surgical facilities are increasingly relying on outsourced processing and supply chain management services to process and supply surgical supplies.

Surgical gowns are worn by surgeons and surgical staff while performing surgical procedures. The primary function of surgical gowns is to provide an adequate liquid barrier to protect the patient, surgeons, and surgical staff. Protecting medical professionals from bodily fluids is critical. While disposable paper gowns are currently in use, manufacturers of those gowns have been forced to add plastic liners to the paper gowns in order to provide an adequate liquid barrier. The plastic liners, however, reduce breathability thereby causing the wearer to be uncomfortably hot. In recent years, new fabrics, such as repellant polyester microfibers and laminated reusable fabrics and materials have been developed for use in reusable gowns. Reusable gowns made of these new fabrics offer greater protection than paper gowns, are comfortable, and durable. As a result, the use of reusable surgical gowns, drapes, surgical towels, back table and mayo stand covers has met with widespread and growing acceptance.

The reusable microfiber fabrics and laminates used in the various reusable textile articles discussed above, require carefully controlled laundering and sterilization between uses in order to properly clean and disinfect the articles while maintaining the integrity of the fabric. Many hospitals simply do not have the facilities necessary to properly clean and sterilize the large number of reusable textiles used, and have been otherwise overburdened by the requirements relating to the management and processing of reusable textiles.

As a result, a number of state-of-the-art processing centers have been built to provide manage and distribute a wide range of reusable textile products to hospitals. It has been found that a most efficient method of providing reusable textile products to hospitals is to maintain a sufficient inventory to support daily delivery and retrieval of reusable textile products. In certain cases reusable articles may be delivered and retrieved to/from the operating room thereby reducing distribution and handling costs incurred by the hospital.

By entrusting an outside vendor with many aspects relating to the management, distribution, and handling of reusable surgical articles hospitals have eliminated many costs associated with the alternative use of disposable articles. For example, bio-hazardous waste handling and disposal costs are substantially eliminated. In addition, the elimination of redundant receiving chores at the receiving dock, central supply, and the operating room was realized. Finally, hospitals were able to substantially reduce their inventory and inventory investment.

Managing and processing large inventories of reusable surgical articles, however, is an enormous and time-consuming task. The large number of articles in inventory requires detailed inventory management and data collection. In addition, reusable textile garments and the like eventually wear out from use and processing and thus have predetermined life cycles. Accordingly, data relating to the number of uses or use cycles for each reusable textile article must be obtained and tracked. Furthermore, reusable gowns, drapes, and the like are often damaged and thus must be visually inspected for the presence of damage, tears, and holes. Lastly, reusable textile articles must be periodically tested to confirm that the fabric retains an important characteristic, namely, resistance or impermeability to liquid.

In an effort to track individual surgical garments among large numbers of said garments attempts have been made to attach bar code labels to each garment for scanning at certain points in the distribution and processing chain. The use of bar code labels to track surgical garments, however, has proven problematic and inefficient. For example, bar code labels are easily damaged or obscured thereby preventing efficient scanning and data entry. In addition, bar code scanning can be time consuming, particularly in view of the time required to locate and properly scan the bar code label on the item.

Similar problems may be experienced in other fields wherein articles are distributed or processed. Attempts have been made to track the locations of portable equipment via radio frequency identification ("RFID") technology. U.S. Pat. No. 5,910,776, issued to Black, discloses the use of RFID transponders to identify and locate equipment in a hospital setting by affixing RFID tags to the electrical cord used for powering the equipment and placing corresponding RFID readers at each electrical outlet. U.S. Pat. No. 6,535,129, issued to Petrick, discloses a system for reducing paperwork by monitoring the chain of custody of medical specimens (e.g. blood samples) as the specimens move from the collection custodians to the laboratory using RFID technology.

While the prior art systems may prove adequate for the limited uses and applications disclosed, there remains a need for an improved inventory management system capable of monitoring use cycles for individual articles of re-usable inventory or non-perishable inventory. There further exists a need for such an inventory management system having data collection and information sharing capabilities such that inventory distributed from multiple remote locations may be effectively managed. There also exists a need for such an inventory management system adapted with RFID technology so as to facilitate real time feedback communication to and from production level employees to assist in managing quality control, inspection, periodic testing, and lifecycle management of reusable inventory.

BRIEF SUMMARY OF THE INVENTION

The present invention contributes to advancements in the art of inventory management and distribution by providing a system and method for processing, distributing, and tracking reusable inventory items. In accordance with the present invention reusable articles, such as surgical garments and accessories, are adapted with radio frequency identification ("RFID") transponders (also referred to as "tags"). In a preferred embodiment, each reusable surgical article is adapted with a passive RFID tag having unique identification information stored thereon. The use of passive tags is considered significant in avoiding RF interference with or from electronic equipment and instruments present in the surgical/hospital environment. RFID is an advanced information acquisition technology that reduces labor, increases read accuracy, and eliminates the line of sight requirement present with bar code systems. Incorporating RFID technology provides a useful method for identifying and tracking a wide range of objects in diverse environments based on the use of a small tag (or "transponder") that stores a unique code. An antenna and coupler are configured to function as a tag "reader". The "reader" emits electromagnetic energy at a specific frequency, which energy causes a tag placed in proximity to the reader to transmit its stored information without requiring direct contact or clear line-of-sight. The reusable articles are processed and distributed using an inventory management system wherein lifecycle data is obtained for each reusable article. The reusable articles are distributed to the end users from multiple central processing facilities, used by the end user, returned, cleaned, inspected, folded, sterilized, and returned to inventory for re-distribution. Each tagged article is electronically read, by an RFID interrogation unit or reader, at one or more stages of processing and the unique identification information corresponding to each tagged article is passed to a computer network. The computer network is adapted to monitor use cycles and to selectively communicate commands directed to personnel responsible for quality control and inspection. For example, the system may indicate the need for routine periodic quality control inspections in response to predetermined usage parameters, or may indicate that the article has reached the end of its lifecycle and should thus be removed from inventory. The use of RFID tags and a corresponding computer network allows for the acquisition of data corresponding to each reusable article within a distribution system having a single, or multiple remote distribution and processing facilities. The acquired data is transmitted to a central computer processing system via a secured wide area communications network for use and analysis. Data processing computer servers at each remote distribution and processing facility electronically linked to a central data processing server provide a fail-safe network for acquired data. The computer network may thus be configured with a central server hub and with each facility configured as a fully functional node in a network wherein data is continuously transmitted from each node to the central server. Accordingly, the present invention may be practiced in a single facility distribution network or a multi-facility distribution network. The continuous polling of data from the node facilities to the central server provides redundant storage of data at the system level, and multiple servers at each node function to mirror data thereby providing local data storage redundancy.

Passing each reusable article in proximity to an RFID reader during one or more phases of processing enables identification of each reusable article and further enables efficiency parameters to be monitored. For example, identifying the number of times that a reusable article has been processed enables the system to prompt facility personnel to conduct quality control inspections after a predetermined number of uses, and to dispose of articles after the useful life has been exhausted. Furthermore, processing efficiency may be evaluated by monitoring the number or articles processed by a facility and/or worker in a given time period. The system also is configured to accept and log feedback information from the production floor for each scanned article. In other applications, multi-read interrogation stations are used to determine the number and type of tagged articles located within a batch of grouped articles, such as surgical packs and instrument sets, thereby improving quality control.

Accordingly, it is an object of the present invention to provide an improved inventory management system.

A further object of the present invention is to provide an inventory management system capable of tracking reusable articles to and from the customer/user.

Another object of the present invention is to provide an inventory management system adapted for tracking inventory in a single or multiple facility distribution and processing network.

Still another object of the present invention is to provide an inventory management system capable of tracking reusable inventory articles throughout expected life cycles.

Yet another object of the present invention is to adapt reusable articles with RFID tags in a multiple facility distribution system such that information relating to the status of tagged articles can be acquired.

A further object of the present invention is to provide an inventory management system wherein the contents of closed packs may be inventoried without requiring that the packs be opened.

In accordance with these and other objects, which will become apparent hereinafter, the instant invention will now be described with particular reference to the accompanying drawings.

DETAILED DESCRIPTION OF THE INVENTION

Figure 1:
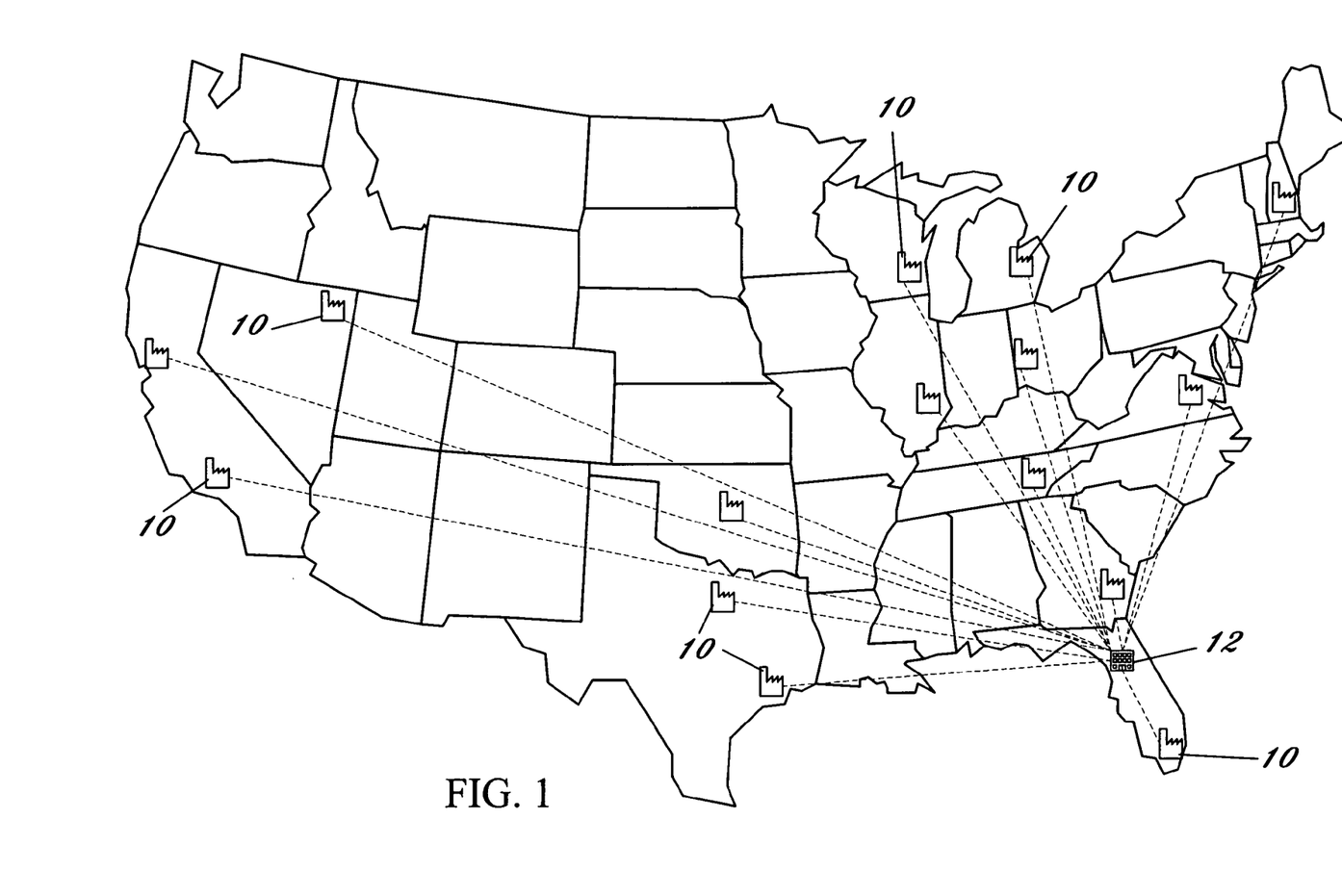
FIG. 1 depicts a multiple facility distribution network having distributed data collection servers in electronic communication with a central server according to preferred embodiment of the present invention.

With reference now to the drawings, FIGS. 1–7 depict a system and method for processing, distributing, and tracking inventory articles in multiple facility distribution network using radio frequency identification ("RFID"). FIG. 1 depicts a multiple facility distribution network wherein a plurality of distribution facilities 10 operate in various geographically remote locations. Each distribution facility 10 electronically communicates with a main office or headquarters, referenced as 12, via a secured wide area computer network. Each distribution facility 10 maintains and distributes an inventory of goods to customers within a specified market, territory, or geographic region. In a preferred embodiment, the goods include medical supplies, and particularly reusable goods such as standard liquid resistant and liquid proof surgical gowns, barrier drapes, liquid proof table covers, towels, mayo instrument stand covers, and equipment draping covers. In an alternate embodiment, the goods may further include reusable surgical instruments and accessories, including autoclavable laparoscopic instruments and light cables, trocar/cannula systems, and stainless steel bowls and accessories. While an RFID inventory management system of the present invention is discussed in the context of reusable surgical articles, the present invention is suitable for use in the distribution and management of any reusable or recyclable goods in any channel of commerce. As used herein the term "reusable article" means any article of inventory subject to multiple distribution and use cycles. As more fully discussed herein below, the system provides an integrated means for tracking reusable inventory within a single or multiple facility network as well as to and from the customer/user.

Figure 2:
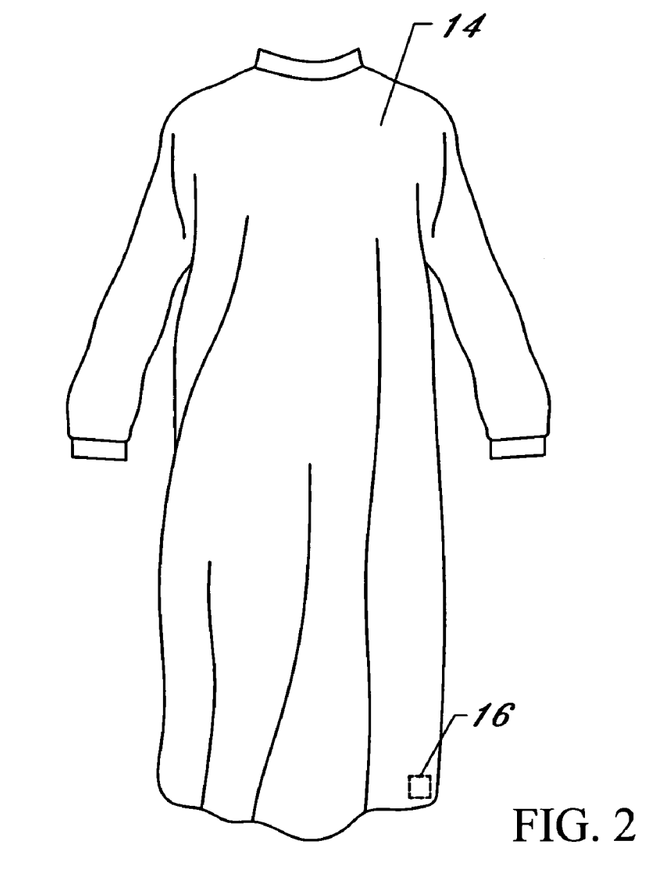
FIG. 2 depicts a reusable surgical gown adapted with an RFID tag.
Figure 3:
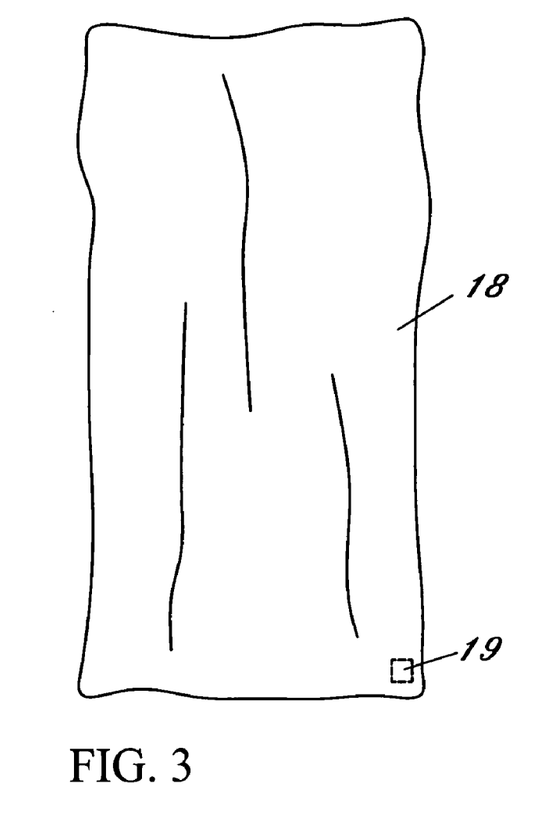
FIG. 3 depicts a reusable surgical drape adapted with an RFID tag.

As illustrated in FIGS. 2 and 3, each reusable article is adapted with an RFID transponder or tag assigned a discrete identification number. In a preferred embodiment, the RFID tags may be sewn into textile articles, such as gowns and drapes, however, any suitable means of attachment is considered within the scope of the present invention. FIG. 2 depicts a typical reusable surgical gown 14 adapted with an RFID tag 16 attached by stitching to a predetermined uniform location, such as the lower right edge of the gown. FIG. 3 depicts a reusable textile surgical drape 18 adapted with an attached RFID tag 19. The RFID tags are preferably passive tags that only function to transmit information stored thereon by inductive coupling when placed within a specific electromagnetic interrogation field generated by an RFID reader at a specified frequency. In a preferred embodiment, the RFID tags and readers are configured to operate at a frequency of approximately 13.56 MHz. A significant aspect of the present invention, relates to the use of RFID tags within a surgical/hospital environment in close proximity to sensitive electronic life safety and monitoring equipment. It has been found that passive RFID tags that operate at a frequency of approximately 13.56 MHz do not effect the operation of hospital equipment and similarly are not effected by the electromagnetic fields generated by hospital equipment. As more fully described herein, the use of RFID tags affixed to reusable articles provides a useful method for identifying and tracking the articles. A "reader" is used both to transmit a signal to a tag and retrieve stored information from it without requiring direct contact or clear line-of-sight. The reusable articles are processed and distributed using an inventory management system wherein lifecycle data is obtained for each reusable article.

Figure 4:
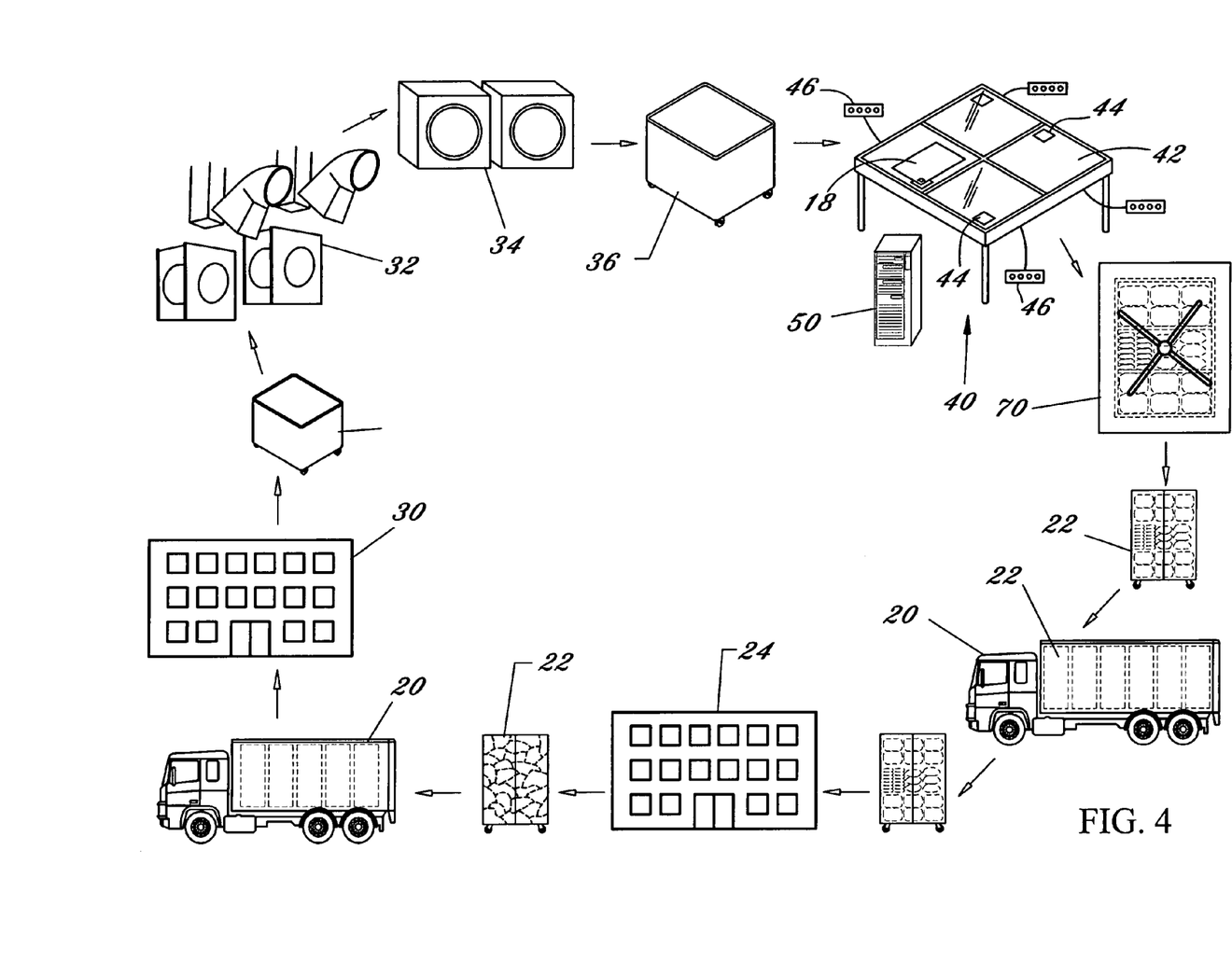
FIG. 4 illustrates a distribution and processing cycle for reusable fabric articles adapted with RFID tags in accordance with the present invention.
Figure 5:
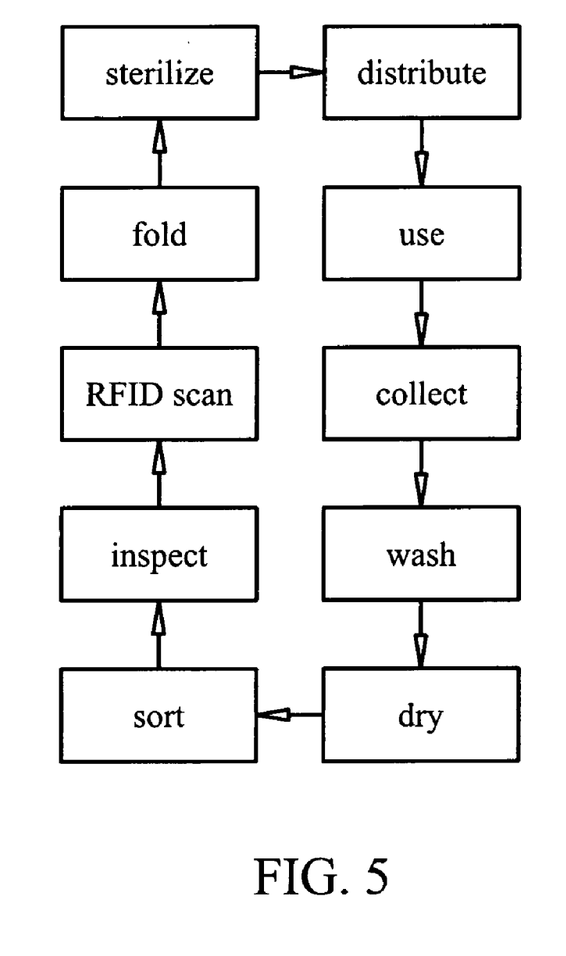
FIG. 5 is a flowchart depicting the distribution and processing cycle for reusable fabric articles.

FIGS. 4 and 5 illustrate a distribution and processing cycle for reusable surgical garments and drapes, generally referenced as 14, adapted with RFID tags. The reusable gowns and drapes are distributed from the distribution facilities 30 by truck 20 or other suitable transport vehicle. In the preferred embodiment, reusable surgical articles are packed and transported a secure cart 22 for use in a hospital 24, or other site where the articles are used, from one of the plurality of processing and distribution facilities. Upon delivery, the gowns, drapes, and other reusable articles, are used by health care professionals while performing surgical procedures. The use of these articles during surgical procedures subjects the articles to biological contamination. Upon completion of the surgical procedure, the used articles are placed back into secure containers 22 for pickup and returned to the processing and distribution facility 30 via truck 20.

Once in the processing facility, the reusable textile articles are sorted prior to being processed. Once sorted, the textile articles are loaded into washing machines 32 for cleaning. Chemicals are injected into the washing machines via a computer controlled injection system. The pH level of the water is intentionally varied between acidic and basic levels to aid in neutralizing biological contaminants. All process water used in cleaning the textile articles, such as surgical gowns and drapes, passes through a sophisticated network of computerized water treatment systems. Upon entering the facility the water is first softened and minerals are removed to precise levels. The water is then routed through a series of heat exchangers wherein the water is preheated using residual latent heat from water exiting the facility. Prior to exiting the facility all wastewater is run through a micromesh filtering system to remove particulates and other fine debris. This combination of computerized water treatment, heat recovery, and filtration results in an energy efficient and environmentally sound process. Upon completion of the washing cycle, the textile articles are subjected to a drying process in drying machines 34.

Upon completion of the drying process, the textile articles are transferred by cart 36 to an inspection and folding area, generally referenced as 40. Each inspection and folding area includes an RFID reader for reading RFID tags attached to the textile articles when the articles are placed on or in proximity to the RFID reader. In a preferred embodiment each inspection and folding area further comprises a light table 42 having a backlit transparent or translucent top upon which the textile articles are placed for inspection and folding. In the preferred embodiment illustrated in FIG. 4, a single inspection table cluster is divided into four folding and inspection stations, referenced as 42A, 42B, 42C, and 42D, thereby accommodating four workers. In an alternate embodiment, a greater or lesser number of stations may be included within the scope of the present invention. The use of backlighting contributes significantly to the inspection process by helping to identify damage to the article, particularly small holes or tears. Each folding and inspection station includes an RFID reader 44 incorporated within the table, preferably immediately below the top surface of table 42. RFID reader 44 is further specifically positioned for communicating with RFID tags attached to a specific location on each of the various textile articles. During the inspection and folding process the workers place each textile article on the inspection and folding area in a uniform manner such that the attached RFID tag is disposed in proximity to the RFID reader thereby enabling inductive coupling and a reading of the articles unique identification number. Accordingly, placing the textile article on the inspection and folding station of light table 42 in a standardized position results in the alignment of and automatic reading of the identification number associated with the article.

Each inspection and folding station includes a worker interface terminal 46 that functions to provide the worker with signals. A first signal, such as the flashing illumination of a green light, confirms that the RFID tag has been successfully read. As discussed herein, the tag is read automatically during the inspection process when the tag is aligned with the read field. A second signal, such as the illumination of a green and red light, indicates that the article has experienced a predetermined number of use cycles that warrant more extensive quality control testing, such as liquid impermeability testing. In addition, the system is adapted for receiving feedback signals generated and transmitted to the network when the inspection worker logs the results of the quality control inspection and testing into the data processing network, such as by depressing a green button indicating "pass" or a red button indicating "fail". A third signal, such as the illumination of a steady green light, indicates that the article is acceptable for further processing and distribution. The worker/inspector is also provided with an RFID or barcode card, or other personal identification apparatus or system that identifies the worker and allows the worker to log damage detected during the inspection process. In addition, the system is configured to generate signals directed to specific articles or groups of articles to the inspection worker. As a result, individual articles may be pulled from the distribution and processing cycle for quality assurance holds, in response to customer input or complaint, or in the event of a recall directed to a particular lot or shipment of articles. Accordingly, the system maximizes the quality of reusable articles maintained within the distribution and processing chain.

Figure 6:
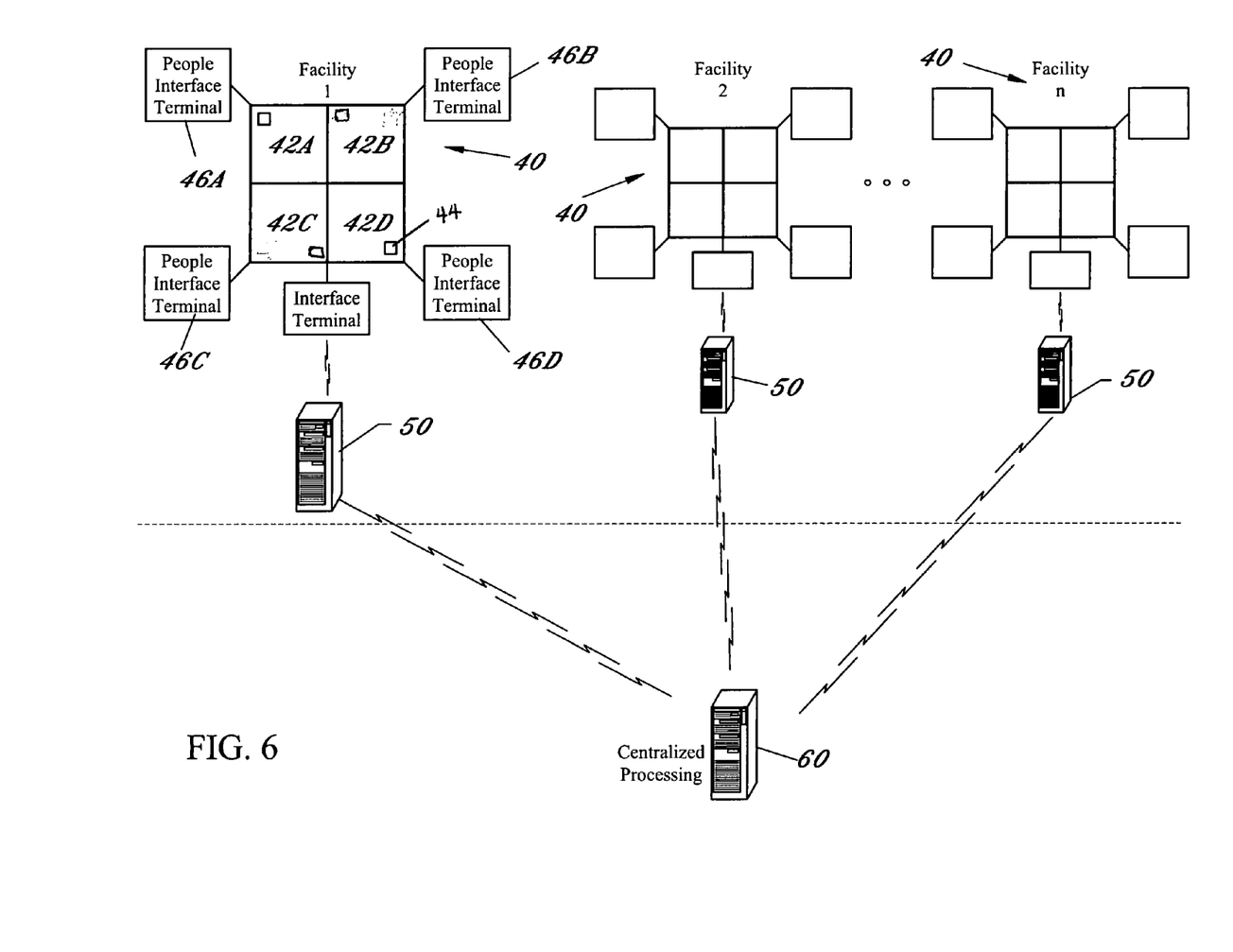
FIG. 6 is a schematic illustration of an RFID a data collection network in accordance with the present invention.

As best illustrated in FIG. 6, each RFID reader at a distribution and processing facility is electronically connected to an on-site computer server 50. The on-site computer server communicates with the various RFID readers and obtains and stores data corresponding to the reusable articles scanned via RFID inductive coupling. Each computer server is in electronic communication with a central processing server 60 that is preferably located at a main office or headquarters. Accordingly, a plurality of facilities 10 are electronically connected via a computer network configured to transmit information obtained by the various RFID readers in the various distribution and processing facility locations. The combination of on-site data processing and storage with centralized/off-site data processing and storage capability provides operational redundancy while enabling centralized control and analysis. For example, if the communication link between a node facility and the central facility is temporarily downed, data continues to be stored and processed at the node facility and is then transmitted to the central server upon restoration of the communication link. The use of RFID tags and corresponding secured wide area network allows for the acquisition of data corresponding to each reusable article within a distribution system having multiple remote distribution and processing facilities. The acquired data is transmitted to a central computer processing system via a secured wide area communications network for use and analysis. Data processing computer servers at each remote distribution and processing facility electronically linked to a central data processing server further provide a fail-safe network for acquired data thereby insuring business continuity. Furthermore, processing efficiency may be evaluated by monitoring the number or articles processed at a particular facility or by a particular worker in a given time period. In addition, washing effectiveness may be evaluated by monitoring the number of articles that require re-washing. Furthermore, the durability of the goods may be evaluated by monitoring the number of damaged articles.

Once the reusable textile articles have been inspected and folded, they are preferably grouped and packaged in standard or customized sets, commonly referred to as "packs", for use in surgical procedures. For example, a typical pack containing reusable surgical articles may include surgical gowns, liquidproof drapes, backtable and mayo stand covers, or any combination of such articles. In alternate embodiments, packs may further comprise surgical instrument sets and accessories. Each pack comprises a set of articles or instruments, grouped and wrapped in a bundle. The outer covering or wrap may comprise a surgical sheet or drape that prevents a visual inspection or confirmation of the contents of the pack. Accordingly, the present invention contemplates providing a multi-read RFID interrogation station configured to enable the identification of each article within each pack prior to distribution.

Once the various packs are formed, they are placed in sterilization chamber 70 wherein the controlled application of heat and pressure functions to render the articles sterile. In a preferred embodiment, sterilization is achieved using a validated Overkill Pre-Vacum Steam Cycle for sterilization with a documented sterilizing assurance level ("SAL") of at least $10^{-6}$. The sterilization process is designed to comply with accepted industry procedures and standards for the sterilization of medical devices, including ANSI/AAMI/ISO 11134 (Sterilization of health care products—Requirements for validation and routine control—Industrial moist heat sterilization), AAMI TIR No. 13 (Principles of Industrial Moist Heat Sterilization), AAMI ISO 11737-2 (Sterilization of medical devices—Microbiological methods—Part 2: Tests of sterility performed in the validation of a sterilized process) and ISO 13863 (Sterilization of health care products—Requirements for the validation and routine control of moist heat sterilization in health care facilities). The packs are preferably loaded into carts 22 for transport to the end user. For example, a typical pack of reusable surgical supplies may include surgical gowns, liquidproof drapes, backtable and Mayo stand covers, as well as stainless steel bowls and surgical instruments. Carts 22, fully stocked with reusable and/or disposable surgical articles are preferably delivered directly to the surgical suite for use.

Figure 7:
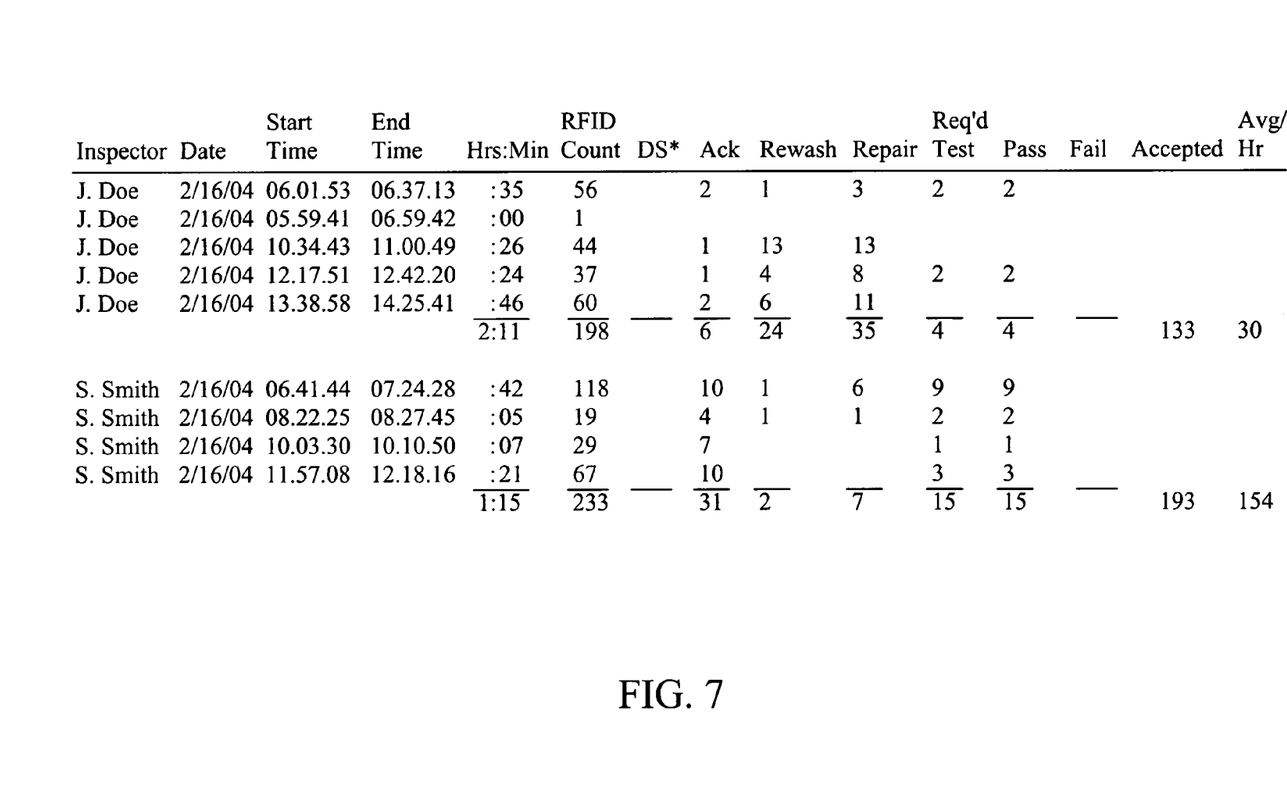
FIG. 7 illustrates information obtained using RFID in the processing of reusable articles.

FIG. 7 illustrates a report generated using information acquired in accordance with the RFID inventory management system disclosed herein. As illustrated in FIG. 7, the efficiency of a facility and/or individual worker may be assessed and monitored. For example, by equipping each worker with a personal RFID card, the system allows for the tracking of work hours/minutes, the number of articles processed, repair rates, etc.

In an alternate embodiment, multi-read interrogation stations may be used to determine the number and type of tagged articles located within a pack, wherein each pack contains one or more articles thereby improving quality control. In this embodiment, individually tagged reusable articles are grouped and bundled or packaged into a pack. As used therein the term "pack" refers to a plurality of tagged articles bundled as a set, which set may include various combinations of articles intended for use in a particular surgical procedure or customized in response to a specific request. Once the pack is bundled, the contents thereof are not subject to visual verification or quality control inspection without disassembly of the pack. Since disassembly of a sterilized pack is effectively a destructive inspection process the present invention relies on multi-read RFID technology to determine the contents. In order to insure that the proper selection and number of reusable articles are contained within a particular pack prior to delivery to the user, the present invention contemplates passing packs through a multi-read antenna array prior to shipment from the distribution and processing facility. Accordingly, the present invention further contemplates an inventory management and distribution system wherein multi-read RFID antennas are used to confirm the contents of prepackaged reusable goods without requiring line of sight verification or otherwise requiring unbundling of sterilized packs. The use of multi-read RFID systems to provide a non-destructive method of determining whether all of the required reusable components are contained within one or more packs designated for shipment provides a significant improvement over prior art inspection methods by eliminating the need for unbundling of individual packs to check and confirm the contents thereby preventing contamination of the sterilized packs.

An additional significant aspect achieved by the present invention relates to monitoring the customers inventory levels. More particularly, the inventory management system of the present invention allows for the monitoring of customer inventory. For example, by tracking the number of articles or packs shipped to a surgical customer and subsequently returned for processing after use, the present invention provides data useful in precisely managing customer inventory thereby preventing over/under stocking of surgical articles.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A method for distributing and processing reusable articles for use in a surgical environment in a medical facility wherein said articles will be contaminated and must be processed after each use to restore them to a condition suitable for reuse in said surgical environment, said method comprising the steps of:

providing a plurality of reusable articles, each reusable article including a respective RFID tag fixedly secured thereto, each tag having a discrete identification number;

utilizing a processing and distribution facility for distributing said reusable articles to a medical facility wherein the articles will be used in a surgical environment, said processing and distribution facility not forming a part of said medical facility and being located remotely therefrom;

utilizing said processing and distribution facility for receiving said reusable articles after use by said medical facility;

processing and decontaminating said received reusable articles at said processing and distribution facility to restore said articles to condition suitable for reuse in a surgical environment;

passing each of said processed and decontaminated reusable articles in proximity to a tag reader at said processing and distribution facility, whereupon said tag reader identifies each of said processed and decontaminated reusable articles by automatically reading the discrete identification number associated with the RFID tag secured thereto;

generating an output signal for each RFID tag read to a computer network, to provide information tracking the number of use cycles for each reusable article;

inspecting each of said reusable articles and generating an other output signal to said computer network, said other output signal corresponding to the physical condition of said reusable article; and utilizing said output signals by said computer network to provide analytic information germane to quality control of at least one of the processing, decontamination, inspection and condition of said reusable articles.

2. The method for distributing and processing reusable articles according to claim 1, wherein said reusable articles comprise textile goods.

3. The method for distributing and processing reusable articles according to claim 2, wherein said textile goods include surgical gowns, surgical drapes, surgical sheets, and equipment covers.

4. The method for distributing and processing reusable articles according to claim 1, wherein said reusable articles comprise surgical instruments.

5. The method for distributing and processing reusable surgical textile articles according to claim 1, further comprising the steps of:

packaging a plurality of said processed and decontaminated reusable articles in individual packs;

passing each of said individual packs in proximity to a multi-read interrogation apparatus that identifies the number and type of processed and decontaminated reusable articles within each individual pack by automatically reading the discrete identification information associated with the attached RFID tag within an individual pack and communicating said identification information to said computer network for verification.

6. The method of claim 1 additionally comprising recording data relating to what is required to be done to the reusable articles for quality control purposes and coordinating that data with the data identifying the reusable articles.

7. The method of claim 6 additionally comprising recording data relating to what processing was done to the reusable articles pursuant to desired quality control practices and coordinating that data with the data identifying the reusable articles.

8. The method of claim 1 additionally comprising recording data relating to what processing was done to the reusable articles pursuant to desired quality control practices and coordinating that data with the data identifying the reusable articles.

9. A method for distributing and processing reusable surgical textile articles for use in surgical environments wherein said articles will be contaminated and must be processed after each use to restore them to a condition suitable for reuse in a surgical environment, said method comprising the steps of:

providing a plurality of reusable textile articles, each reusable textile article including a respective RFID tag fixedly secured thereto, each tag having discrete identification information;

distributing said reusable articles to a medical facility wherein the articles will be used in a surgical procedure;

receiving said distributed reusable textile articles at a processing and distribution facility not forming a part of said medical facility and being located remotely therefrom after said articles have been used in at least one surgical procedure;

decontaminating said received reusable textile articles at said processing and distribution facility;

inspecting said decontaminated reusable textile articles for damage at said processing and distribution facility;

passing each of said decontaminated reusable textile articles in proximity to a tag reader at said processing and distribution facility to automatically identify each of said decontaminated reusable textile articles by reading the discrete identification information associated with the attached RFID tag;

outputting an output signal including the discrete identification information for each RFID tag detected to a computer network thereby tracking the number of use cycles for each reusable article;

said computer network generating a signal indicating a need for quality control testing of a decontaminated reusable article in response to data indicating the decontaminated reusable article has experienced a predetermined number of use cycles;

folding said decontaminated reusable textile articles;

sterilizing said decontaminated reusable textile articles; and utilizing said computer network to provide analytic information germane to quality control of at least one of the processing, decontamination, inspection and condition of said reusable textile articles.

10. An inventory tracking and control system for tracking and controlling the distribution of reusable articles for use in a surgical environment in a medical facility wherein said articles will be contaminated and must be processed after each use to restore them to a condition suitable for reuse in said surgical environment, said system comprising:

a processing and distribution facility;

said processing and distribution facility not forming a part of said medical facility and being located remotely therefrom, said processing and distribution facility having an inventory consisting of a plurality of reusable articles, each of said articles including a respective RFID tag fixedly secured thereto, each tag having a discrete identification number;

means for distributing said reusable articles to said medical facility wherein said reusable articles will be used in said surgical environment;

means for receiving said reusable articles after use by in said surgical environment;

means for processing and decontaminating said received reusable articles to restore said articles to condition suitable for reuse;

means for passing each of said processed and decontaminated reusable articles in proximity to a tag reader that identifies each of said processed and decontaminated reusable articles by automatically reading the discrete identification number associated with the RFID tag secured thereto; and means for outputting an interrogation output signal for each RFID tag detected to a computer network for tracking the number of use cycles for each reusable article, said computer network being arranged to provide analytic information germane to quality control of at least one of the processing, decontamination, inspection and condition of said reusable articles.

11. The inventory tracking and control system according to claim 10 wherein said reusable articles comprise textile articles and wherein said system further comprises:

means for decontaminating said received reusable textile articles.

12. The inventory tracking and control system according to claim 10, further comprising:

means for inspecting said decontaminated reusable textile articles for damage.

13. The inventory tracking and control system according to claim 10, further comprising:

means for generating a signal indicating a need for quality control testing of a reusable article when the article has experienced a predetermined number of use cycles.

14. An inventory tracking and control system for tracking and controlling the distribution of reusable articles from multiple distribution and processing facilities, each of said articles being arranged for use in a surgical environment in a medical facility wherein said articles will be contaminated and must be processed after each use to restore them to a condition suitable for reuse in said surgical environment, said system comprising:

a plurality of processing and distribution facilities;

each of said plurality of processing and distribution facilities having an inventory consisting of a plurality of reusable articles, each of said reusable articles including a respective RFID tag fixedly secured thereto, each tag having a discrete identification number;

each of said processing and distribution facilities not forming a portion of said medical facility and being located remotely therefrom, each of said processing and distribution facilities including means for distributing said reusable articles to a medical facility wherein said reusable articles will be used in a surgical environment;

each of said processing and distribution facilities including means for receiving said reusable articles returned after use in said surgical environment;

each of said processing and distribution facilities including means for processing and decontaminating said received reusable articles to restore said received reusable articles to a condition suitable for reuse in said surgical environment;

each of said processing and distribution facilities including means for passing each of said processed and decontaminated reusable articles in proximity to a tag reader that identifies each of said processed and decontaminated reusable articles by automatically reading the discrete identification number associated with the RFID tag secured thereto; and each of said distribution facilities including means for generating an output signal for each RFID tag detected to a computer network for tracking the number of use cycles for each reusable article;

said computer network being arranged to provide analytic information germane to quality control of at least one of the processing, decontamination, inspection and condition of said reusable articles and including a computer data processing and data storage system located at each of said plurality of distribution facilities;

said computer network further including a central computer data processing and data storage system;

each of said computer data processing and data storage systems located at each of said plurality of processing and distribution facilities being in electronic communication with said central computer data processing and data storage system.

15. The inventory tracking and control system according to claim 14, further comprising means for generating a signal indicating a need for quality control testing of a reusable article when the article has experienced a predetermined number of use cycles.

16. A method for processing reusable articles for use in a surgical environment in a medical facility, wherein said articles will be contaminated and must be processed after each use at a processing and distribution facility by cleaning to restore them to a condition suitable for reuse in said surgical environment, said processing and distribution facility not forming a portion of said medical facility and being located remotely therefrom, said method comprising:

providing a plurality of said reusable articles disposed within a sealed package at said processing and distribution facility, at least two of said reusable articles each including an RFID tag permanently secured thereto, each of said tags being arranged to respond to a transmitted electromagnetic signal by producing an output signal indicative of a unique identifier of said reusable article to which said tag is secured;

passing said package to a multi-read interrogation station at said processing and distribution facility;

transmitting an electromagnetic signal into an interrogation region at said multi-read interrogation station, whereupon each of said tags produces an output signal indicative of a unique identifier of said reusable article to which said tag is secured; and receiving said output signals from said at least two reusable articles in said package to identify the at least two reusable articles within said package and to provide information tracking the number of use cycles for each of the at least two reusable articles.

17. The method of claim 16 wherein each of said reusable articles has been used in a surgical procedure in said surgical environment, and wherein said method additionally comprises:

processing and decontaminating said reusable articles after their usage in said surgical procedure; and disposing said processed and decontaminated reusable articles in said package.

18. The method of claim 17 wherein at least one of said reusable articles comprises a fabric article.

19. The method of claim 17 wherein at least one of said reusable articles comprises an instrument.

20. The method of claim 17 additionally comprising inspecting said articles after said articles are processing and decontaminated.

21. A system for processing reusable articles for use in a surgical environment in a medical facility, wherein said reusable articles will be contaminated and must be processed after each use by cleaning and sterilization to restore them to a condition suitable for reuse in said surgical environment, said system comprising:

a plurality of said reusable articles, at least two of said reusable articles each including an RFID tag permanently secured thereto and being disposed within a sealed package;

a multi-read interrogation station located at a processing and distribution facility not forming a portion of said medical facility and being located remotely therefrom; and a computer;

said multi-read interrogation station comprising at least one antenna, said at least one antenna being arranged for transmitting an electromagnetic signal into an interrogation region at said station, each of said tags being arranged when in said interrogation region to respond to said electromagnetic signal by producing an output signal indicative of a unique identifier of said reusable article to which said tag is secured, said sealed package being arranged to be brought to said interrogation region, said at least one antenna being arranged to receive said output signals from said at least two articles in said package for use by said computer to identify said at least two articles within said package and to provide information tracking the number of use cycles for each of said at least two reusable articles within said package.

22. The system of claim 21 wherein said at least one of said articles comprises a fabric article.

23. The system of claim 21 wherein said at least one of said articles comprises an instrument.

* * * * *